United States Patent [19]

McAmish et al.

[11] Patent Number: 4,908,163

[45] Date of Patent: Mar. 13, 1990

[54] NONWOVEN MEDICAL FABRIC

[75] Inventors: Larry H. McAmish; Tralance O. Addy, both of Arlington, Tex.; George F. Lee, Greer, S.C.

[73] Assignee: Surgikos, Inc., Arlington, Tex.

[21] Appl. No.: 884,563

[22] Filed: Jul. 11, 1986

Related U.S. Application Data

[62] Division of Ser. No. 763,508, Aug. 8, 1985, Pat. No. 4,622,259.

[51] Int. Cl.⁴ .............................................. B29B 9/00
[52] U.S. Cl. ...................................... 264/12; 156/167; 264/284; 264/293; 264/517; 264/518
[58] Field of Search ............... 156/167, 181, 209, 290, 156/308.4, 311; 428/903; 264/12, 517, 518, 284, 293

[56] References Cited

U.S. PATENT DOCUMENTS 2,988,469 6/1961 Watson .................................. 264/12
4,100,324 7/1978 Anderson et al. .................. 156/167

Primary Examiner—James J. Bell
Attorney, Agent, or Firm—Lawrence D. Schuler

[57] ABSTRACT

A nonreinforced microfiber fabric is disclosed. The fabric has minimum grab tensile strength to weight ratio greater than 0.8 N per gram per square meter and a minimum Elmendorf tear strength to weight ratio greater than 0.04 N per gram per square meter. The fibers in the fabric have an average length greater than 10 centimeters and at least 80% of the fibers have a diameter of 7 microns or less. The fabric is made by thermally embossing a microfiber web which is made with a minimum of degradation to the polymer and employing high velocity secondary air to maintain air flow uniformity and fiber length.

11 Claims, 2 Drawing Sheets

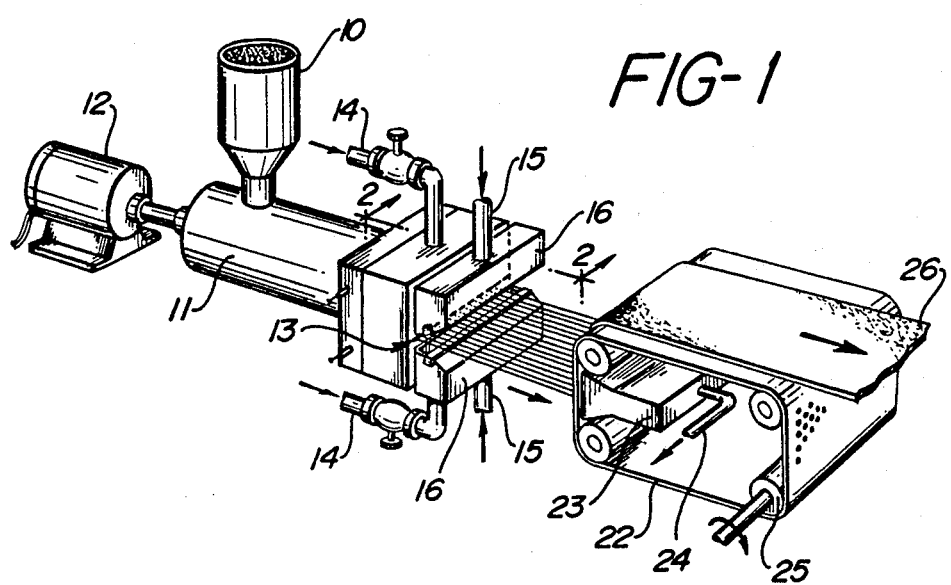
FIG-1
FIG-2
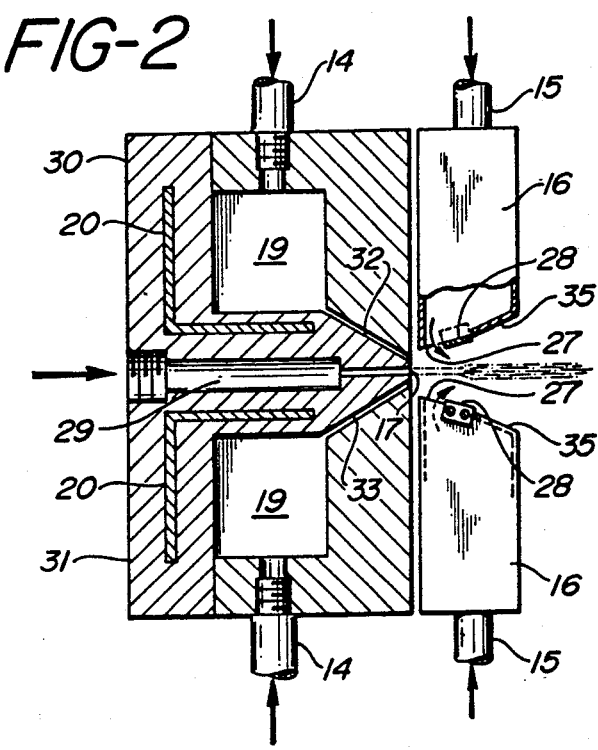
FIG-3
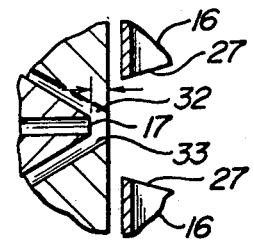
FIG-4
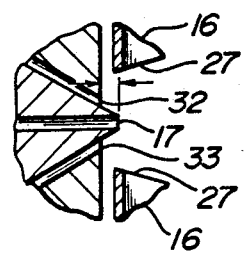

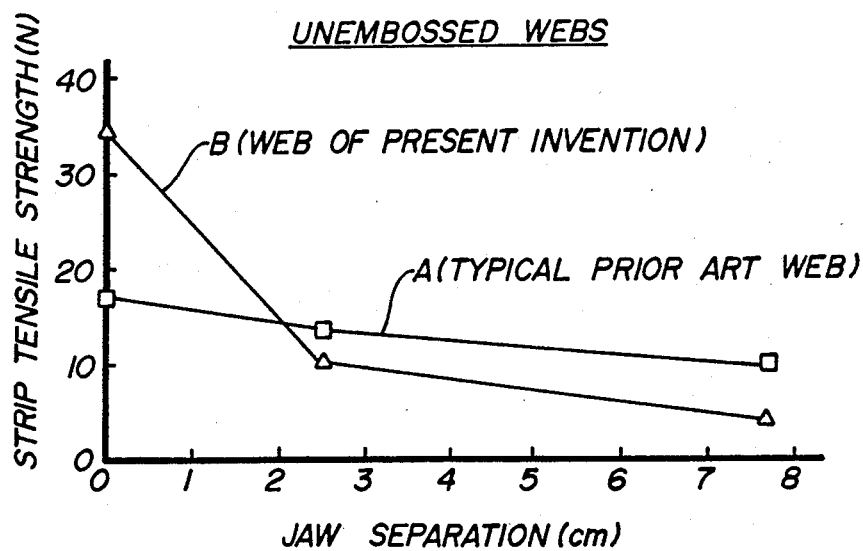
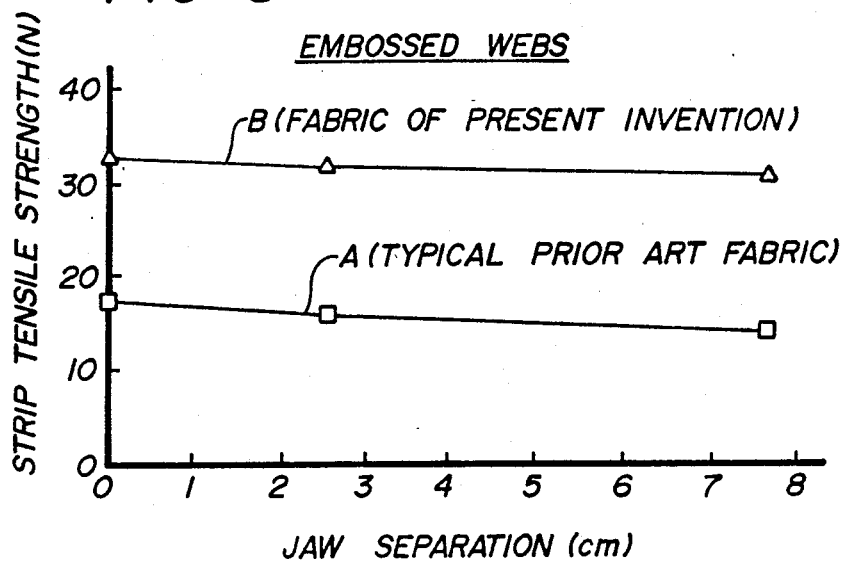

NONWOVEN MEDICAL FABRIC

This is a division of application Ser. No. 763,508, filed Aug. 8, 1985, now U.S. Pat. No. 4,622,259.

FIELD OF THE INVENTION

The present invention relates to nonwoven fabrics made of unreinforced microfiber webs, characterized by high strength, and especially suitable for use as medical fabrics.

BACKGROUND OF THE INVENTION

The present invention is directed to nonwoven fabrics and particularly to medical fabrics. The term "medical fabric", as used herein, is a fabric which may be used as the fabric for surgical drapes, surgical gowns, instrument wraps, or the like. Such medical fabrics have certain required properties to insure that they will perform properly for the intended use. These properties include strength, the capability of resisting water or other liquid penetration, often referred to as strike-through resistance, as well as being breathable, soft, drapable, sterilizable and a bacterial barrier.

In important areas, some of these characteristics or attributes appear to be in direct opposition to one another in a given fabric, and consequently, conventional disposable medical fabrics have not achieved an optimum balance of the desired attributes. For instance, with prior art fabrics which are comprised predominantly of spunbonded webs, random-laid staple fiber webs, tissue and scrim laminates, spunlaced webs, or combinations thereof, attempts to improve the key repellency or barrier properties invariably compromise breathability and softness attributes. Thus, those fabrics with superior breathability and other aesthetic attributes tend to be relatively inferior in strike-through resistance. As a further example, in order to improve strength, it is generally known to increase the weight of the fabric, compact the web to a high degree, add or increase binders, or adopt various combinations of these techniques. However, such attempts often result in undesirable aesthetic characteristics, as the resulting fabrics tend to be generally stiffer and less breathable.

The use of microfiber webs in applications where barrier properties are desired is known in the prior art. Microfibers are fibers having a diameter of from less than 1 micron to about 10 microns. Microfiber webs are often referred to as melt-blown webs as they are usually made by a melt blowing process. It is generally recognized that the use of relatively small diameter fibers in a fabric structure should allow the achievement of high repellency or filtration properties without undue compromise of breathability. Microfiber web fabrics made heretofore, and intended for use as medical fabrics, have been composites of microfiber webs laminated or otherwise bonded to spunbonded thermoplastic fiber webs, or films, or other reinforcing webs which provide the requisite strength to the fabric. The microfiber, melt-blown webs heretofore developed have been reported to possess insufficient strength, when unreinforced, to be used in medical or other applications where high strength at relatively low weights is desirable or important. For example, in the "Journal of Industrial Fabrics", Vol. 3, No. 1, 1984, pages 33-44, it is indicated that the most serious deficiency of melt-blown webs is their strength per unit weight when compared to conventional webs or scrims of the same material. Japanese patent application Disclosure 180, 653-1983 indicates that melt-blown sheets lack tensile strength and attributes this deficiency to the fact that the melt-blown sheets are formed of undrawn fibers. United Kingdom patent application Disclosure G.B. No. 2104562A, discloses that other fibrous reinforcements are necessary to impart strength to melt-blown webs for use as medical fabrics. U.S. Pat. No. 4,041,203 discloses a nonwoven fabric made by combining microfiber webs and spunbonded webs to produce a fabric useful as a medical fabric. The patent gives various examples demonstrating the necessity of reinforcing melt-blown webs to provide adequate strength. Example 1 of the patent describes a thermally point-bonded melt-blown web before and after addition of a spunbonded reinforcement layer. The grab tensile strength to basis weight ratio of the embossed unreinforced melt-blown web was lower than can be used for medical fabrics at practical weight levels. The patent further specifically discloses various webs made with polypropylene. The microfiber webs and the continuous-filament, polypropylene, spunbonded webs are laminated together through the application of heat and pressure in a pattern to produce a medical fabric. The continuous-filament, spunbonded web provides the strength to the laminated fabric.

U.S. Pat. No. 4,302,495 discloses a laminate of a microfiber web and a directionally-oriented thermoplastic netting. The thermoplastic netting provides the requisite strength to the finished nonwoven fabric.

U.S. Pat. No. 4,196,245 discloses combinations of melt-blown or microfine fibers with apertured films or with apertured films and spunbonded fabrics. Again, the apertured film and the spunbonded fabric are the components in the finished, nonwoven fabric which provide the strength to the fabric.

While the above-mentioned fabrics have the potential to achieve a better balance of repellency and breathability compared to other prior art technologies not using microfibers, the addition of reinforcement layers of relatively large diameter fibers limits their advantages. The fabrics have to be assembled using two or more web forming technologies, resulting in increased process complexity and cost. Furthermore, the bonding of relatively conventional fibrous webs to the microfibers can result in stiff fabrics, especially where high strength is desired.

BRIEF SUMMARY OF THE INVENTION

The present invention seeks to avoid the limitations of the above-mentioned prior art fabrics by providing a medical fabric from an unreinforced web or webs of microfine fibers. The present fabric is unreinforced in that it need not be laminated or bonded to another type of web or film to provide adequate strength to be used in medical applications. The fabric of the present invention also achieves a balance of repellency, strength, breathability and other aesthetics superior to prior art fabrics.

The requirements for medical grade fabrics are quite demanding. The fabric must have sufficient strength to resist tearing or pulling apart during normal use, for instance, in an operating room environment. This is especially true for fabrics that are to be used for operating room apparel such as surgical gowns or scrub suits or for surgical drapes. One measure of the strength of a nonwoven fabric is the grab tensile strength. The grab tensile strength is generally the load necessary to pull apart or break a 10 cm wide sample of the fabric.

The test for grab tensile strength of nonwoven fabrics is described in ASTM D1117. Nonwoven medical fabrics must also be resistant to tearing. The tearing strength or resistance is generally measured by the Elmendorf Tear Test as described in ASTM D1117. As an example, the grab tensile strengths, measured in the weakest, normally cross machine direction, of the least strong commercially used medical fabrics are in the range of 45 newtons (N) with tear strengths in the weakest direction of approximately 2N. At these levels of strength, fabric failure can often occur in fabrics during use as gowns and drapes, and it is generally desired to achieve higher strength levels. Grab tensile strength levels of approximately 65 N and above and tear resistance levels of approximately 6N and above would allow a particular medical fabric to be used in a wider range of applications. It is an objective of the present invention to provide a fabric with high strength to weight ratio, such that at desirable weights, both grab tensile and tear strengths higher than the above values can be achieved. The fabrics of the present invention generally have basis weights in the range of 14 to 85 g/m$^2$.

Medical fabrics must also be repellent to fluids including blood, that are commonly encountered in hospital operating rooms. Since these fluids offer a convenient vehicle for microorganisms to be transported from one location to another, repellency is a critical functional attribute of medical fabrics. A measure of repellency that is influenced primarily by the pore structure of a fabric is the "hydrostatic head" test, AATCC 127-1977. The hydrostatic head test measures the pressure, in units of height of a column of water, necessary to penetrate a given sample of fabric. Since the ultimate resistance of a given fabric to liquid penetration is governed by the pore structure of the fabric, the hydrostatic head test is an effective method to assess the inherent repellent attributes of a medical fabric. Nonwoven medical fabrics which do not include impermeable films or microfiber webs generally possess hydrostatic head values between 20 to 30 cm of water. It is generally recognized that these values are not optimum for gowns and drapes, especially for those situations in which the risk of infection is high. Values of 40 cm or greater are desirable. Unfortunately, prior art disposable fabrics which possess high hydrostatic head values are associated with low breathability or relatively low strength. It is another objective of the present invention to provide a fabric which can attain a high level of fluid repellency.

The breathability of medical fabrics is also a desirable property. This is especially true if the fabrics are to be used for wearing apparel. The breathability of fabrics is related to both the rate of moisture vapor transmission (MVTR) and air permeability. Since most fibrous webs used for medical fabrics possess reasonably high levels of MVTR, the measurement of air permeability is an appropriate discriminating quantitative test of breathability. Generally the more open the structure of a fabric, the higher its air permeability. Thus, highly compacted, dense webs with very small pore structures result in fabrics with poor air permeability and are consequently perceived to have poor breathability. An increase in the weight of a given fabric would also decrease its air permeability. A measure of air permeability is the Frazier air porosity test, ASTM D737. Medical garments made of fabrics with Frazier air porosity below 8 cubic meters per minute per square meter of fabric would tend to be uncomfortable when worn for any length of time. It is a further objective of the present invention to provide a fabric which achieves good breathability without sacrifice of repellency or strength.

Medical fabrics must also have good drapability, which may be measured by various methods including the Cusick drape test. In the Cusick drape test, a circular fabric sample is held concentrically between horizontal discs which are smaller than the fabric sample. The fabric is allowed to drape into folds around the lower of the discs. The shadow of the draped sample is projected onto an annular ring of paper of the same size as the unsupported portion of the fabric sample. The outline of the shadow is traced onto the annular ring of paper. The mass of the annular ring of paper is determined. The paper is then cut along the trace of the shadow, and the mass of the inner portion of the ring which represents the shadow is determined. The drape coefficient is the mass of the inner ring divided by the mass of the annular ring times 100. The lower the drape coefficient, the more drapable the fabric. Drapability correlates well with softness and flexibility.

In addition to the above characteristics, medical grade fabrics must have anti-static properties and fire retardancy. The fabrics should also possess good resistance to abrasion, and not shed small fibrous particles, generally referred to as lint.

The present invention provides a melt blown or microfiber fabric which has adequate strength and tear resistance, without reinforcement, to be used as a medical fabric and in other applications where high strength and tear resistance are required. The embossed fabrics of the present invention have a minimum grab tensile strength to weight ratio of at least 0.8N per gram per square meter and a minimum Elmendorf tear strength to weight ratio of at least 0.04N per gram per square meter. These strength properties are achieved while also obtaining the properties of repellency, air permeability and drapability that are desired for the use of the fabric in medical applications.

In addition to the strength characteristics mentioned above, the fabric of the present invention differs from prior art melt blown webs in that the average length of the individual fibers in the web is greater than the average length of the fibers in prior art webs. The average fiber length in the present webs is greater than 10 cm, preferably greater than 20 cm and most preferably in the range of 25 to 50 cm. Also, the average diameter of the fibers in the web should be no greater than 7 microns. The distribution of the fiber diameters is such that at least 80% of the fibers have a diameter no greater than 7 microns and preferably at least 90% of the fibers have a diameter no greater than 7 microns.

In the description of the present invention the term "web" refers to the unbonded web formed by the melt blowing process. The term "fabric" refers to the web after it is bonded by heat embossing or other means.

BRIEF DESCRIPTION OF THE DRAWINGS

FIG. 1 is an isometric view of the melt-blowing process.

FIG. 2 is a cross-sectional view of the placement of the die and the placement of the secondary air source.

FIG. 3 is a detailed fragmentary view of the extrusion die illustrating negative set back.

FIG. 4 is a detailed fragmentary view of the extrusion die illustrating positive set back.

FIG. 5 is a graph comparing the effects of gauge length on the strip tensile strength of two samples of unembossed webs.

FIG. 6 is similar to FIG. 5 except that the plot is for point-bonded thermally embossed fabrics of the webs of FIG. 5.

DETAILED DESCRIPTION OF THE INVENTION

As shown in FIG. 1, the process of the present invention is carried out in conventional melt-blowing equipment which has been modified to provide high velocity secondary air. In the apparatus shown, a thermoplastic resin in the form of pellets or granules, is fed into a hopper 10. The pellets are then introduced into the extruder 11 in which the temperature is controlled through multiple heating zones to raise the temperature of the resin above its melting point. The extruder is driven by a motor 12 which moves the resin through the heating zones of the extruder and into the die 13. The die 13 may also have multiple heating zones. The resin passes from the extruder into a heater chamber 29 which is between the upper and lower die plates 30 and 31. The upper and lower die plates are heated by heaters 20 to raise the temperature of die and the resin in the chamber 29 to the desired level. The resin is then forced through a plurality of minute orifices 17 in the face of the die. Conventionally, there are about 12 orifices per centimeter of width of the die. An inert hot gas, usually air, is forced into the die through lines 14 into gas chamber 19. The heated gas, known as primary air, then flows to gas slots 32 and 33 which are located in either side of the resin orifices 17. The hot gas attenuates the resin into fibers as the resin passes out of the orifices 17. The width of the slot 32 or 33 is referred to as the air gap. The fibers are directed by the hot gas onto a web forming foraminous conveyor 22 to form a mat or web 26. It is usual to employ a vacuum box 23 attached to a suitable vacuum line 24 to assist in the collection of the fibers. The screen 22 is driven around rollers 25 so as to form a web continuously. In the present process, the fibers are contacted by high velocity secondary air immediately after the fibers exit the die. The secondary air is ambient air at room temperature or at outside air temperature. If desired, the secondary air can be chilled. The secondary air is forced under pressure from an appropriate source through feed lines 15 and into distributor 16 located on each side of the die. The distributors are generally as long as the face of the die. The distributors have an angled face 35 with an opening 27 adjacent the die face. The velocity of the secondary air can be controlled by increasing the pressure in feed line 15 or by the use of a baffle 28. The baffle would restrict the size of the opening 27, thereby increasing the velocity of air exiting the distribution box, at constant volume. The outlets of the orifices 17 and the gas slots 32 and 33 may be in the same plane or may be offset. FIG. 3 shows the orifice 17 terminating inward of the face of the die and the slots 32 and 33. This arrangement is referred to as negative setback. The setback dimension is shown by the space between the arrows in FIG. 3. Positive setback is illustrated outward of the face of the die and the slots 32 and 33. The setback dimension is shown by the space between the arrows in FIG. 4. A negative setback is preferred in the present process as it allows greater flexibility in setting the air gap without adversely effecting the quality of the web produced.

The present nonwoven fabric differs from prior art microfiber-containing fabrics in the utilization of the melt-blowing process to produce microfibers with characteristics which result in uniquely high fabric strength to weight ratios, if the fibers are formed into a web and thermally bonded as described herein.

In the practice of prior art melt-blown technology for fabric related applications, it is typical to produce microfibers which range in average diameter from about 1 to 10 microns. While in a given web, there may be a range of fiber diameters, it is often necessary to keep the diameters of these fibers low in order to fully exploit the advantages of microfiber structures as good filtration media. Thus, it is usual to produce webs or batts with average fiber diameters of less than 5 microns or at times even less than 2 microns. In such prior art processes, it is also typical for such fibers to be of average lengths between 5 to 10 centimeters (cm). As discussed in the review of the prior art fabrics, the webs formed from such fibers have very low strength. The tensile strength of such a web is primarily due to the bonding that occurs between fibers as they are deposited on the forming conveyor. Some degree of interfiber surface bonding can occur because in the conventional practice of melt-blown technology, the fibers may be deposited on the forming conveyor in a state in which the fibers are not completely solid. Their semi-molten surfaces can then fuse together at cross-over points. This bond formation is sometimes referred to as autogenous bonding. The higher the level of autogenous bonding, the higher the integrity of the web. However, if autogenous bonding of the thermoplastic fibers is excessively high, the webs become stiff, harsh and quite brittle. The strength of such unembossed webs is furthermore not adequate for practical applications such as medical fabrics. Thermal bonding of these webs can generally improve strength. However, as discussed in previous sections, without introduction of substantial amounts of reinforcing elements such as other types of fibers, binders, etc., it has heretofore not been possible to produce melt-blown microdenier fabrics with high strength, particularly for use as surgical gowns, scrub apparel and drapes, where tensile and tear strengths are important.

In forming the webs of the fabric of the present invention, fibers are produced which are longer than fibers of the prior art. Fiber lengths were determined using rectangular-shaped wire forms. These forms had span lengths ranging from 5 to 50 cm in 5 cm increments. Strips of double-faced adhesive tape were applied to the wire to provide adhesive sites to collect fibers from the fiber stream. Fiber lengths were determined by first passing each wire form quickly through the fiber stream, perpendicular to the direction of flow, and at a distance closer to the location of the forming conveyor than to the melt blowing die. Average fiber lengths were then approximated on the basis of the number of individual fibers spanning the wire forms at successive span lengths. Applicants have discovered that if a substantial portion of the fibers are longer than 10 cm, such that the average fiber length is at least greater than 10 cm and preferably greater than 20 cm, the webs, thus formed, can result in embossed fabrics with unique strength, while maintaining other desired features of a medical fabric. Fabrics with highly desirable properties are produced when average fiber lengths are in the range of 25 to 50 cm. In order to maintain the potential of microdenier fibers to resist liquid penetration, it is necessary to keep the diameters of the fibers low. In order to develop high repellency, it is necessary for the average diameter of the fibers of the present fabric to be no greater than 7 microns. At least 80% of the fibers should have diameters no greater than 7 microns. Preferably, at least 90% of the fibers should have diameters no greater than 7 microns. A narrow distribution of fiber diameters enhances the potential for achieving the unique balance of properties of this invention. While it is possible to produce fabrics with average fiber diameters greater than 7 microns and obtain high strength, the ultimate repellency of such a fabric would be compromised, and it would then not be feasible to produce low weight fabrics with high repellency.

Applicants have further discovered that when the melt-blown fibrous web is formed in such a manner that autogenous bonding is very low and the webs have little or no integrity, the fabrics that result upon thermal embossing these webs are much stronger and possess better aesthetics than fabrics made of webs with high initial strength. That is, the weakest unembossed webs, with fiber dimensions as described above, form the strongest embossed fabrics. The higher the level of initial interfiber bonding, the stiffer and more brittle the resulting fabric, leading to poor grab and tear strengths. As autogenous bonding is reduced, the resulting fabric develops not only good strength but becomes softer and more drapable after thermal embossing. Because of the relatively low levels of web integrity, it is useful to determine the strength of the unembossed web by the strip tensile strength method, which uses a 2.54 cm-wide sample and grip facings which are also a minimum 2.54 cm wide (ASTM D1117). In prior art melt blown fabrics the machine direction (MD) strip tensile strength of the autogenously bonded web is generally greater than 30% and frequently up to 70% or more of the strip tensile strength of the bonded fabric. That is, the potential contribution of autogenous bonding to the strength of the embossed fabric is quite high. In the present invention autogenous bonding contributes less than 30%, and preferably less than 10%, of the strip tensile strength of the bonded fabric.

For example, a Nylon 6 melt-blown web with a weight of approximately 50 g/m$^2$ made under prior art conditions may possess a strip tensile strength in the machine direction of between 10 to 20N. In the fabric of this invention, it is necessary to keep the strip tensile strength of the unembossed web below 10N and preferably below 5N to achieve the full benefits of the invention. In other words, when long fibers are produced and collected, in such a way that initial interfiber bonding is low, the individual fibers are stronger, and there is greater exploitation of the inherent strength of the fibers themselves.

While it is difficult and tedious to obtain an accurate determination of the strength of individual microdenier fibers, a good reflection of the strength of the fibers can be obtained by using the zero-span strip test method. In the normal strip tensile test, the load cells are set at approximately 7.6 cm apart. At this span length, the application of modest loads in the machine direction to an unembossed web may cause the web to fail from fibers slipping by one another rather than by actually breaking the fibers. This is particularly true if the strength of the individual fibers is much higher than the strength of the autogenous bond. The integrity is then due primarily to the interfiber bonding, i.e., autogenous bonding, and perhaps partially to the length of the fibers and their degree of entanglement. As the span length is decreased, there is a smaller and smaller chance for the fibers to move, and at very short distances, close to zero span, the lengths of the fibers, and interfiber movements, are no longer factors in the values measured. The strength of the individual fibers and the ultimate strength of the fabric.

FIG. 5 illustrates the phenomena described above, and indicates the advantage of achieving high individual fiber strength, and low interfiber bonding of the unembossed web. The plot shows the relationship between breaking strength (strip tensile) and span length for two Nylon 6 melt-blown webs of approximately the same weight, one of which, "A", was produced with characteristics typical of conventional melt-blown processes, and the other, "B", was produced under conditions and with characteristics typical of the present invention. The normal strip tensile test shows "A" to be stronger than "B" by over 300% (11.1N vs. 3.5N). At zero span length, the strengths have crossed over, and the tensile strength of "B" is greater by about 93% over "A" (35N vs. 18.1N). This indicates that the individual fibers of the webs of the present invention are stronger than the individual fibers of the webs of the prior art. FIG. 6 serves as a further illustration demonstrating that the strength of embossed fabric "B" is greater than the strength of embossed fabric "A". At the normal strip tensile span (7.6 cm), the strength of "B" is almost 200% that of "A" (30.5N vs. 15.8N). The processes of preparing "A" and "B" are set forth in Example I. The zero span strip tensile strength to weight ratio in the machine direction (M.D.) of the fabrics of the present invention is greater than 0.4N.m$^2$/g and preferably greater than 0.5 N.m$^2$/g. For fabric applications where very high strengths are required, the zero span strip tensile strengths to weight ratio should be greater than 1.0 N.m$^2$/g.

In summary, the web of the fabric of the present invention, in contrast to conventional melt-blown webs of the prior art, is characterized by high average fiber length, low interfiber bonding and stronger individual fibers. These characteristics are achieved while maintaining low fiber diameters in a relatively narrow distribution range to provide high resistance to fluid penetration. High aesthetic characteristics are also obtained.

The method of producing the desired web characteristics of the fabric of the invention is based on the control of the key process variables and their interactions to achieve the desired fiber, web, and fabric properties. These process variables include extrusion temperatures, primary air flow and temperature, secondary air flow, and forming length. Since there are many combinations of these factors which can produce different aspects of the present fabric, the influence of these variables on the key desired web properties will now be described in general.

As previously discussed, in order to obtain strong melt-blown fabrics, the individual fibers themselves should possess good strength. In conventional melt-blowing processes, it is generally recommended that the resin in the extruder and die should be maintained at a high enough temperature to degrade the polymer extensively so as to improve polymer flow and avoid the formation of "shot". Shot is defined as a mass of nonfibrous polymer with a diameter greater than 0.3 mm. Typically, the die melt temperature, i.e., the temperature of the polymer melt at the die, is about 100° C. above the melting temperature of the resin. However, excessive degradation of the polymer reduces the potential to form individual fibers with high strength. Applicants have determined that individual fiber strength can be enhanced significantly if the die melt temperature, for instance, can be maintained at levels generally 10° to 35° C. below temperatures recommended for prior art processes. Generally, in the present process the die melt temperature is no greater than about 75° C. above the melting point of the polymer. Obviously, the specific optimum temperature would depend on the polymer being extruded. In general, the level of degradation must be kept as low as possible without forming shot. By proper design of the melt-blowing die, and control of forming air to fiber ratios, shot formation can be avoided or substantially reduced.

The strength of the individual fiber is also dependent on the degree of molecular orientation that is achieved when the extruded fiber is attenuated by the air stream. The rate of attenuation and the rate of cooling of the fibers are, therefore, important. The velocity and temperature of the primary air, and the velocity and temperature of the secondary air must be adjusted to achieve optimum fiber strength, zero span strength, for a given polymer. The high velocity secondary air employed in the present process is instrumental in increasing the time and the distance over which the fibers are attenuated. The cooling effect of the secondary air enhances the probability that the molecular orientation of the fibers is not excessively relaxed on the deceleration of the fibers as they are collected on the screen.

The achievable fiber length also is influenced by the primary and secondary air velocities, the level of degradation of the polymer and, of critical importance, air flow uniformity. In forming the web of the fabric of this invention, it is of extreme importance to maintain a high degree of air and fiber flow uniformity, avoiding large amplitude turbulence, vortices, streaks, and other flow irregularities. Good primary air flow uniformity can be obtained by adhering to standard aerodynamic design guidelines in the design of die air plenums and nozzles. In a conventional melt-blowing process, as the primary air velocity increases and fiber diameters decrease, the fibers are more easily ruptured by high amplitude turbulence. By maintaining high uniformity, breakage of the fibers is minimized and optimum fiber lengths can be achieved. Introduction of high velocity secondary air also serves to control the air/fiber stream, by cooling and maintaining molecular orientation of the fibers so that stronger fibers are produced that are more resistant to possible breakage caused by nonuniform air flow.

In order to deposit the fibers on the forming conveyor as a web with low strip tensile strength, the forming air and forming distance are clearly important. In the present process, the forming distance is generally between 20 and 50 centimeters. First, in order for the web to have minimal interfiber bonding, the fibers must arrive at the forming conveyor in a relatively solid state, free of surface tackiness. To allow the fibers time to solidify, it is possible to set the forming conveyor farther away from the die. However, at excessively long distances, i.e., greater than 50 cm., it is difficult to maintain good uniformity of the air/fiber stream and "roping" may occur. Roping is a phenomenon by which individual fibers get entangled with one another in the air stream to form coarse fiber bundles. Excessive roping diminishes the capacity of the resultant fabric to resist fluid penetration, and also leads to poor aesthetic attributes. A primary air flow of high uniformity enhances the opportunity to achieve good fiber attenuation and relatively long distance forming without roping.

The primary air volume is also an important factor. Sufficient air volume must be used, at a given polymer flow rate and forming length, to maintain good fiber separation in the air/fiber stream, in order to minimize the extent of roping.

The use of the secondary air system also is important in achieving low interfiber bonding without roping. As noted previously, the high velocity secondary air is effective in improving the uniformity of the air/fiber stream. Thus, it enhances the potential to move the forming length beyond prior art distances, without causing undesirable roping. Furthermore, since the secondary air is maintained at ambient temperature, or lower if desired, it can serve also to cool and solidify the fibers in a shorter time, thus obviating the need for detrimentally large forming lengths. For the secondary air system to have an influence on flow uniformity and cooling, and the rate of deceleration of the fibers, its velocity should be high enough that its flow is not completely overwhelmed by the primary air flow. In the present process, a secondary air velocity of 30 m/sec to 200 m/sec or higher is effective in providing the desired air flow characteristics.

Obviously, there are various approaches and combinations of primary and secondary air flows, temperatures, and forming lengths that can be used to achieve low interfiber bonding in the unembossed web. The specific process parameters depend on the polymer being used, the design of the die and its air systems, the production rate, and the desired product properties.

The unembossed web or layers of unembossed webs must be bonded to convert the web or webs to a fabric to be used in applications requiring good integrity. It has been determined to be advantageous to use thermal bonding techniques. Either ultrasonic or mechanical embossing roll systems using heat and pressure may be used. For the present invention, it is preferred to use a mechanical embossing system for point bonding using an engraved roll on one side and a solid smooth roll on the other side of the fabric. In order to avoid "pinholes" in the fabric, it has also been found desirable to set a small gap, of the order of 0.01 mm, between the top and bottom rolls. For the intended use of the fabrics which can be produced by this invention, the total embossed area must be in the range of 5 to 30% of the total fabric surface, and preferably should be in the range of 10–20%. In the examples given to illustrate the invention, the embossed area is 18%. The embossing pattern is 0.76 mm×0.76 mm diamond pattern with 31 diamonds per square centimeter of roll surface. The particular embossing pattern employed is not critical and any pattern bonding between 5 and 30% of the fabric surface may be used.

In order to render the fabric especially effective for use in applications requiring high abrasion resistance, a small amount of chemical binder can be applied by suitable means to the surface of the fabric in small quantities. i.e., less than 10% of fabric weight. An example of such a binder is Primacor 4990 which is an 80/20 copolymer of ethylene and acrylic acid, manufactured by the Dow Chemical Company. For applications requiring repellency, such as for surgical gowns and drapes, the fabric can be treated further with suitable repellent chemicals. Fluorochemicals are normally employed to impart repellency.

The principles of this invention apply to any of the commercially available resins, such as polypropylene, polyethylene, polyamides, polyester or any polymer or polymer blends capable of being melt blown. It has been found particularly advantageous to use polyamides, and particularly Nylon 6 (polycaprolactam), in order to obtain superior aesthetics, low susceptibility to degradation due to cobalt irradiation, excellent balance of properties, and overall ease of processing.

Generally, the fabrics of the present invention have a basis weight of from 14 to 85 grams per square meter. The fabrics have a minimum grab tensile strength to weight ratio greater than 0.8N per gram per square meter and a minimum Elmendorf tear strength to weight ratio greater than 0.04N per gram per square meter. For medical fabrics where high strength is required, the fabrics have a basic weight no greater than 60 grams per square meter and have a minimum grab tensile strength of 65N and a minimum Elmendorf tear strength not less than 6N.

It is to be understood that the fibers, webs or fabrics produced according to this invention can be combined in various ways, and with other fibers, webs, or fabrics possessing different characteristics to form products with specifically tailored properties.

The examples which follow are intended to clarify further the present invention, and are in no way intended to serve as the limits of the content or scope of this invention.

EXAMPLE 1

Three one-ply melt-blown nylon webs of approximately 50 g/m$^2$ were produced, using for Fabric A, specifications typical of prior art processes. Fabrics B and C were produced using process conditions and fiber and web characteristics typical of the present invention. All three fabrics were then embossed under identical conditions, again with typical settings of the present invention. The strengths of these fabrics were then compared:

| Process Parameters | | Fabric A | Fabric B | Fabric C |
|---|---|---|---|---|
| Die melt temperature (°C.) | | 315 | 280 | 264 |
| Primary air temperature (°C.) | | 334 | 318 | 285 |
| Air gap/setback (cm) (neg) | | .178/.178 | .114/.102 | .114/.102 |
| Polymer flow per cm of die width (g/min) | | 4.8 | 1.7 | 1.7 |
| Secondary air velocity (m/sec) | | 0 | 30 | 30 |
| Forming length (collector distance) (cm) | | 22 | 22 | 22 |
| Top embossing roll temperature (°C.) | | 99 | 103 | 97 |
| Bottom embossing roll temperature (°C.) | | 97 | 98 | 99 |
| Roll separation gap (mm) | | 0.01 | 0.01 | 0.01 |
| Fabric Properties | | | | |
| Grab tensile strength to weight ratio (N · m$^2$/g) | MD | 0.67 | 1.43 | 1.72 |
| | CD | 0.50 | 0.96 | 1.04 |
| Elmendorf tear strength to weight ratio (N · m$^2$/g) | MD | 0.03 | 0.22 | 0.18 |
| | CD | 0.04 | 0.31 | 0.24 |

Fabrics B and C had superior strength, in both grab tensile and tear strength. In particular, the tear strengths of B and C were dramatically improved over prior art expectations.

EXAMPLE 2

In this example, variations in the method to produce the fabric of this invention were used to illustrate the structural characteristics of the fabric of this invention compared with a fabric based on the same process conditions as specified for Fabric A in Example 1.

All fabrics were produced using single-ply Nylon 6 webs with approximate weight of 50 g/m$^2$.

Fabric A was produced under conditions exemplified in Example 1 (Fabric A). Fabrics D through H were produced under conditions typical of the present invention, all at lower die melt temperatures (264°–280° C.) and high velocity secondary air using various combinations of primary air volume and velocity and secondary air velocity. The strength characteristics of the fabrics were then compared.

| | | Fabric | | | | | |
|---|---|---|---|---|---|---|---|
| Parameter | | A | D | E | F | G | H |
| Avg. fiber length (cm) | | 10 | 25 | 25 | 46 | 20 | 46 |
| Avg. fiber diameter (cm) | | 2.0 | 3.7 | 5.6 | 4.3 | 3.5 | 4.3 |
| Grab tensile strength: | | | | | | | |
| Ratio (N · m$^2$/g) | MD | .67 | 1.33 | 1.43 | 1.76 | 1.45 | 1.72 |
| | CD | .50 | 1.07 | .96 | 1.21 | .84 | 1.04 |
| Tear strength ratio: | | | | | | | |
| Ratio (N · m$^2$/g) | MD | .03 | .20 | .22 | .15 | .08 | .18 |
| | CD | .04 | .25 | .31 | .28 | .16 | .24 |

All of the fabrics produced using conditions described in this application possess not only longer fiber length, but higher strength as well, compared to Fabric A.

EXAMPLE 3

Single-ply Nylon 6 microfiber webs were formed under two different conditions to illustrate the effect of low initial interfiber bonds of the unembossed web on the strength properties of the embossed fabric. Fabric A in this example is the same web and fabric as Fabric A of Example 1, representing prior art melt-blown web structure. Fabric B is the same as Fabric B of Example 1. The two webs were similar in weight of about 50 g/m$^2$. The zero-span strength plots of these webs are shown in FIG. 5.

| Parameter | | | Fabric A | Fabric B |
|---|---|---|---|---|
| Strip Tensile Strength (Unembossed) | (N) | MD | 11.1 | 3.5 |
| Zero Span Strip Tensile (Unembossed) | (N) | MD | 18.1 | 35 |
| Strip Tensile (Embossed) | (N) | MD | 15.8 | 30.5 |
| Grab Tensile Strength (Embossed) | (N) | MD | 31.6 | 73.0 |
| | | CD | 23.5 | 49.0 |
| Tear Strength (Embossed) | (N) | MD | 1.3 | 11.1 |
| | | CD | 1.7 | 14.8 |

The web of Fabric B, with very low initial strip tensile, surprisingly yielded a fabric with excellent strength and aesthetic properties after embossing.

EXAMPLE 4

In order to illustrate the effect of temperature on the strength of melt-blown fabrics, two single-ply nylon webs were produced using identical conditions except for temperature. Thus, the die melt temperature of the web for Fabric "K" was 20° C. lower than for Fabric "J". The webs were also embossed under identical conditions with an embossed area of 18% of the total fabric surface.

| Parameter | | Fabric J | Fabric K |
|---|---|---|---|
| Polymer rate per cm of width (g/min) | | 1.7 | 1.7 |
| Die melt temperature (°C.) | | 294 | 274 |
| Basis weight (g/m²) | | 46 | 46 |
| Grab tensile strength (N) | MD | 71 | 107 |
| | CD | 61 | 80 |
| Intrinsic viscosity (dl/g) | | 1.09 | 1.28 |

As observed, lower temperatures enhance the strength of the fabric as degradation of the polymer is kept at lower levels than standard practice. The intrinsic viscosity values confirm that the polymer in Fabric K was degraded less. The intrinsic viscosity was determined using 90% formic acid at 25° C.

EXAMPLE 5

Melt-blown polypropylene webs were produced, first using typical conditions described in the prior art to obtain webs of conventional structural characteristics. Then, webs were produced using the principles of the present invention. Also, a combination of the two different webs was assembled. All the webs were thermally embossed under identical conditions to produce fabrics. Fabric L was produced under conditions in the range of prior art processes. The web for Fabric M was produced using the principles of the present invention. Fabric N was produced by laminating a 34 g/m² layer of web M to a 13.5 g/m² layer of Web L. Fabric O is an example of the properties of a prior art thermally embossed polypropylene melt-blown web as described in U.S. Pat. No. 4,041,203. Example 1. Fabric P was produced under the same conditions as Fabric L, but with high velocity secondary air.

| Process conditions | | Fabric | | | | |
|---|---|---|---|---|---|---|
| | | L | M | N | O | P |
| Die melt temperature (°C.) | | 279 | 260 | — | — | 279 |
| Primary air temperature (°C.) | | 315 | 272 | — | — | 315 |
| Primary air velocity (m/sec) | | 278 | 153 | — | — | 278 |
| Polymer flow rate per cm (g/min) | | 1.7 | 1.7 | — | — | 1.7 |
| Forming length (collector distance) (cm) | | 15 | 48 | — | — | 15 |
| Die air gap (mm) | | 1.14 | 1.14 | — | — | 1.14 |
| Die setback (mm) negative | | 1.02 | 1.02 | — | — | 1.02 |
| Secondary air velocity (m/sec) | | 0 | 30 | — | — | 30 |
| Fabric Characteristics | | | | | | |
| Grab tensile strength to weight ratio (N · m²/g) | MD | 0.69 | 1.13 | 1.03 | 0.46 | .91 |
| | CD | 0.47 | 0.93 | 0.88 | — | .84 |
| Elmendorf tear strength to weight ratio (N · m²/g) | MD | .002 | .178 | .050 | — | .005 |
| | CD | .003 | .300 | .098 | — | .007 |
| Trapezoidal tear | | | | | | |

-continued

| Process conditions | | Fabric | | | | |
|---|---|---|---|---|---|---|
| | | L | M | N | O | P |
| strength to weight ratio (N · m²/g) (ASTM D117) | MD | .011 | .499 | .384 | .087 | .052 |
| | CD | .025 | .876 | .601 | — | .120 |

Particularly dramatic is the improvement in tear strength demonstrated by Fabrics M and N, far exceeding values obtained with prior art technology.

This example also illustrates that various combinations of different webs can be laminated to produce a variety of fabric properties.

EXAMPLE 6

As described in preceding sections, for gown and drape applications, the requirements of a good fabric are quite demanding. After producing the embossed fabric, it normally has to be further treated to render it repellent in order to resist penetration by the normal fluids encountered in its use. Normally, fluorochemical finishes are employed to impart repellency.

For illustration, a single-ply Nylon 6 web was produced under the following conditions:

| Die melt temperature | 267° C. |
|---|---|
| Primary air temperature | 289° C. |
| Primary air velocity | 227 m/sec |
| Polymer flow rate | 1.7 g/min/cm |
| Collector distance | 27 cm |
| Die air gap | 1.14 mm |
| Die set back negative | 1.02 mm |
| Secondary air velocity | 30 m/sec |

The weight was approximately 49 g/m². The fabric was sprayed with a fluorochemical solution (Scotchguard) at a level of 5 grams per square meter and dried. The properties of this fabric in key aspects were then compared with those of other fabrics commercially used or available as medical fabrics. In this example, Fabric 1 represents the fabric of this invention, Fabric 2 is produced by hydraulically entangling polyester staple fibers with pulp fibers. It is commercially available under the trademark "Sontara" and manufactured by the E. I. du Pont de Nemours & Company of Wilmington, Delaware. It is widely used as a medical fabric. Fabric 3 is produced by thermally emboss-laminating continuous fiber (spunbonded) polypropylene web layers on both sides of a melt-blown polypropylene layer. The fabric is commercially used as a medical fabric under the trademark "Spunguard", manufactured by Kimberly-Clark Corporation of Neenah, Wisconsin. Fabric 4 is an example of a wood pulp/polyester blended nonwoven fabric available from the C. H. Dexter Corporation as Assure III. Fabric 5 is a three-component laminate comprising two plies of tissue around a layer of spunbonded nylon core. The fabric has been used as a medical fabric and commercially available as "Boundary—Fabric III". Fabric 6 is another example of a laminate structure with outside layers of tissue on each side of a scrim core. The fabric is trademarked "Regard", manufactured by Kimberly-Clark. It has been used commonly as a medical fabric. Fabric 7 is a low denier thermally embossed spunbonded polyethylene fabric manufactured by E. I. du Pont under the tradename "Tyvek". It is available and has been used as a medical fabric.

| Fabric | W | HH | GTS* | TS* | FAP | TH | CDC |
|---|---|---|---|---|---|---|---|
| 1 | 52 | 49 | 81 | 10 | 18 | .32 | 44 |
| 2 | 75 | 25 | 69 | >16 | 24 | .34 | 45 |
| 3 | 49 | 42 | 50 | 2 | 11 | .32 | 70 |
| 4 | 69 | 26 | 75 | >16 | 24 | .25 | 92 |
| 5 | 75 | 24 | 60 | 6 | 12 | .29 | 65 |
| 6 | 75 | 25 | 53 | >6 | 6 | .34 | 78 |
| 7 | 48 | 75 | 66 | 16 | 1 | .20 | 80 |

*Weakest direction
NOTE:
W: Basis weight (g/m$^2$)
HH: Hydrostatic head (cm. H$_2$O)
GTS: Grab tensile strength (N)
TS: Elmendorf tear strength (N)
FAP: Frazier air porosity (m$^3$/min-m$^2$)
TH: Thickness (mm)
CDC: Cusick drape coefficient (%)

The ideal medical fabric would, of course, have high hydrostatic head, high strength, high breathability, low weight (especially for gowns), with high bulk so as not to be "flimsy" in use as drapes, and low Cusick drape coefficient. Because of inherent limitations, and as illustrated in the above table, most fabrics achieve one desirable charcteristic only at considerable expense of other important characteristics. In order to facilitiate comparison of the properties shown in the table, and to evaluate the balance of properties achieved by each fabric, the absolute value of each property can be normalized such that for each fabric characteristic, the fabric with the highest value can be assigned a value of 1. All other fabrics will then have properties reflected as fractions of the highest value. A normalized chart is shown in the following table.

| Fabric | W | HH | GTS | TS* | FAP | TH | CDC |
|---|---|---|---|---|---|---|---|
| 1 | .69 | .65 | 1.00 | .63 | .75 | .64 | .48 |
| 2 | 1.00 | .33 | .85 | 1.00 | 1.00 | 1.00 | .49 |
| 3 | .65 | .56 | .62 | .13 | .46 | .94 | .76 |
| 4 | .92 | .35 | .93 | 1.00 | 1.00 | .74 | 1.00 |
| 5 | 1.00 | .32 | .74 | .38 | .50 | .85 | .71 |
| 6 | 1.00 | .33 | .65 | .38 | .25 | 1.00 | .85 |
| 7 | .64 | 1.00 | .82 | 1.00 | .04 | .59 | .87 |

A performance index of each fabric can now be computed from the ratio:

$$\frac{GTS \times HH \times TS \times FAP \times \text{Thickness}}{WT \times CDC}$$

The performance indices are listed below:

| Fabric | Performance Index |
|---|---|
| 1 | .88 |
| 2 | .57 |
| 3 | .04 |
| 4 | .26 |
| 5 | .05 |
| 6 | .02 |
| 7 | .04 |

These indices demonstrate the unique and superior balance of properties achieved by the present invention, compared to prior art fabrics.

We Claim:

1. In a method of producing a nonreinforced meltblown microfiber embossed fabric wherein a fiber-forming thermoplastic polymer resin in molten form is forced through a row of orifices in a heated die into a primary stream of inert gas to attenuate the resin into fibers, and the fibers are collected on a receiver to form a web, and the web is thermally bonded to form a fabric, the improvement which comprises: maintaining the polymer melt temperature at a level which minimizes molecular degradation, controlling the velocity, volume and temperature of said primary stream of inert gas to produce fibers at least 80% of which have a diameter of 7 microns or less and having an average length of more than 10 centimeters, introducing a highly uniform high velocity secondary stream of inert gas in quantities sufficient to cool the fibers and maintain good fiber separation, collecting the fibers at a forming distance which results in a web with low interfiber bonding, prior to embossing the web to form a fabric.

2. The method according to Claim 1, where the polymer melt temperature at the die is no greater than 75° C. above the melting temperature of the polymer.

3. The method according to Claim 1, where the velocity of said secondary stream of inert gas is at least 30 m/sec.

4. The method according to Claim 1, where the average fiber length in the unembossed web is greater than 20 cm.

5. The method of Claim 1 in which at least 90% of the fibers have an average diameter of 7 microns or less.

6. The method of Claim 1 in which the web is thermally embossed at intermittent discrete bond regions which occupy between 5 and 30% of the surface of the fabric.

7. The method of Claim 6 in which the bond regions occupy between 15 and 25% of the surface of the fabric.

8. The method of Claim 1 in which the autogenous bonding of the fibers in the web contributes no more than 30% of the strip tensile strength of the embossed fabric.

9. The method of Claim 8 in which the autogenous bonding of the fibers in the web contributes no more than 10% of strip tensile strength of the embossed fabric.

10. The method of Claim 1 wherein said high velocity secondary air is introduced immediately after said fibers exit said die.

11. The method of Claim 1 wherein the velocity, volume and temperature of said primary stream of inert gas are controlled to provide fibers whose average lengths are in the range of 25 to 50 centimeters.

* * * * *